United States Patent [19]
Chaffee et al.

[11] Patent Number: 4,633,872
[45] Date of Patent: Jan. 6, 1987

[54] LASER OPTICAL DELIVERY APPARATUS

[75] Inventors: Edwin G. Chaffee; Steve Holtman, both of Salt Lake City; George A. Nelson, Sandy; Howard M. C. Tanner, Salt Lake City, all of Utah

[73] Assignee: HGM, Incorporated, Salt Lake City, Utah

[21] Appl. No.: 549,819

[22] Filed: Nov. 8, 1983

[51] Int. Cl.⁴ .................................... A61B 17/36
[52] U.S. Cl. .................... 128/303.1; 211/121 LR
[58] Field of Search ........... 128/4, 6, 303.1, 395–398; 219/121 LA, 121 LQ, 121 LR, 121 LU

[56] References Cited

U.S. PATENT DOCUMENTS

| | | | |
|---|---|---|---|
| 3,703,176 | 11/1972 | Vassiliadis et al. | 128/395 |
| 3,914,013 | 10/1975 | Rosenberg | 128/303.1 |
| 4,309,998 | 1/1982 | Aron nee Rosa et al. | 128/395 |
| 4,433,675 | 2/1984 | Keroshim | 128/6 |
| 4,476,512 | 10/1984 | Sanago et al. | 128/303.1 |
| 4,517,974 | 5/1985 | Tanner | 128/303.17 |
| 4,520,816 | 6/1985 | Schachar et al. | 128/395 |
| 4,526,170 | 7/1985 | Tanner | 128/398 |
| 4,537,193 | 8/1985 | Tanner | 128/303.1 |

FOREIGN PATENT DOCUMENTS 0075912 4/1983 European Pat. Off. ......... 128/303.1

Primary Examiner—Edward M. Coven
Assistant Examiner—Max F. Hindenburg
Attorney, Agent, or Firm—B. B. Olive

[57] ABSTRACT

An improved optical delivery assembly for an argon-ion or similar medical laser attaches to a wobble plate for thermal tracking and supports in a single integral subassembly an adjustable focusing lens, a beam splitter and associated light detector enabling selective display of power at both proximal and distal ends of the fiber, scattering and blocking shutters, a scattering shutter position sensor, shutter control solenoids, an optical plug position sensor and an optical plug mounting block adapted to interchangeably receive any of several types of optical fiber connecting plugs.

10 Claims, 19 Drawing Figures

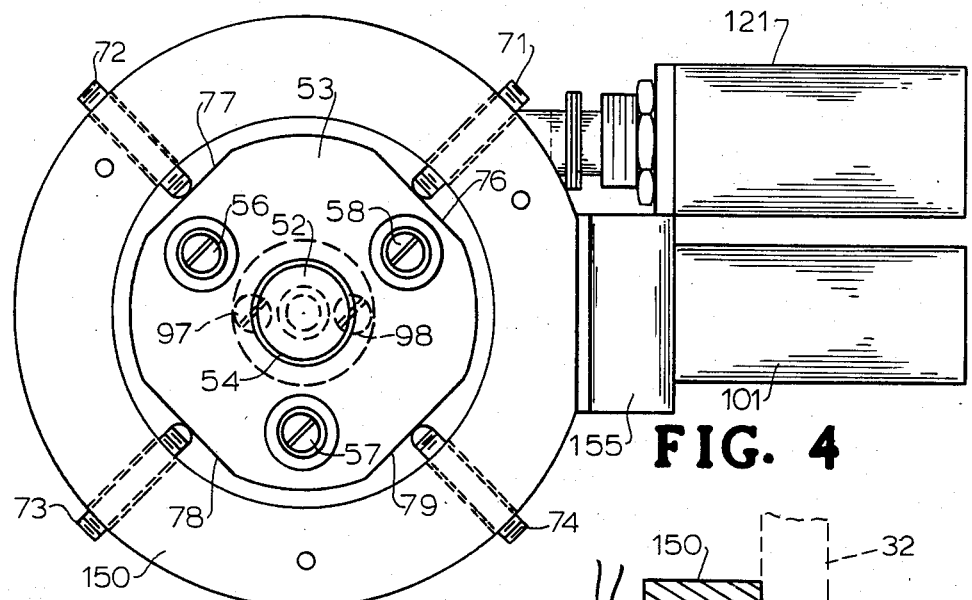
FIG. 4
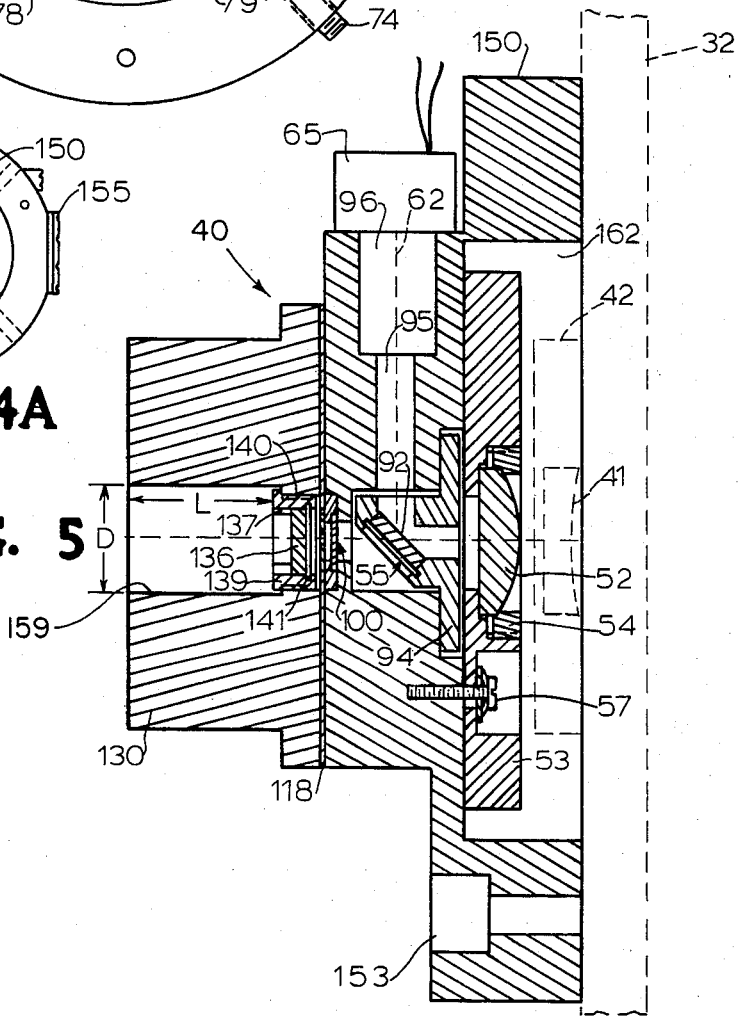
FIG. 4A
FIG. 5

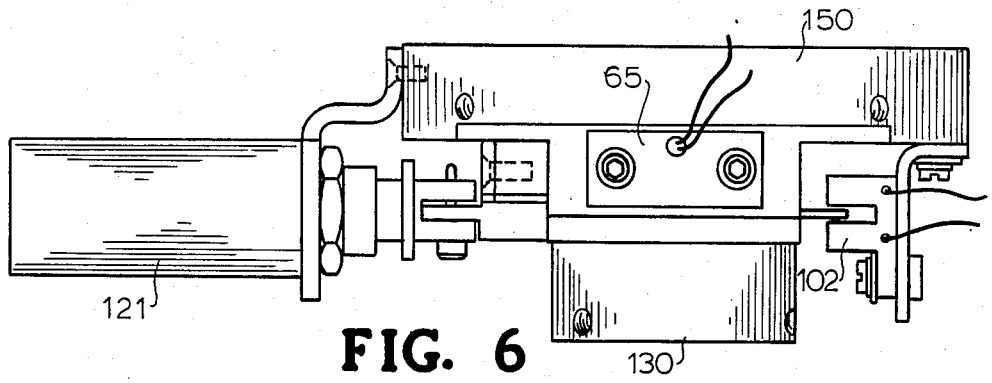
FIG. 6
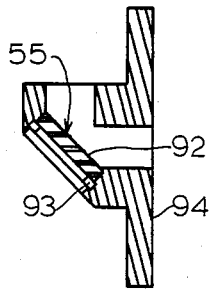
FIG. 7
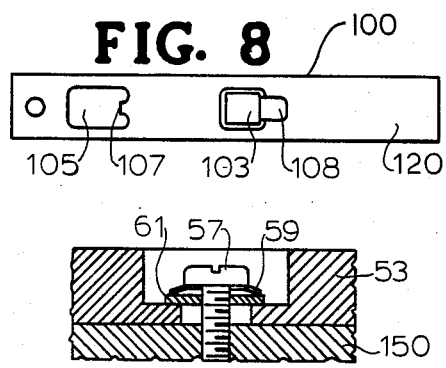
FIG. 8
FIG. 9
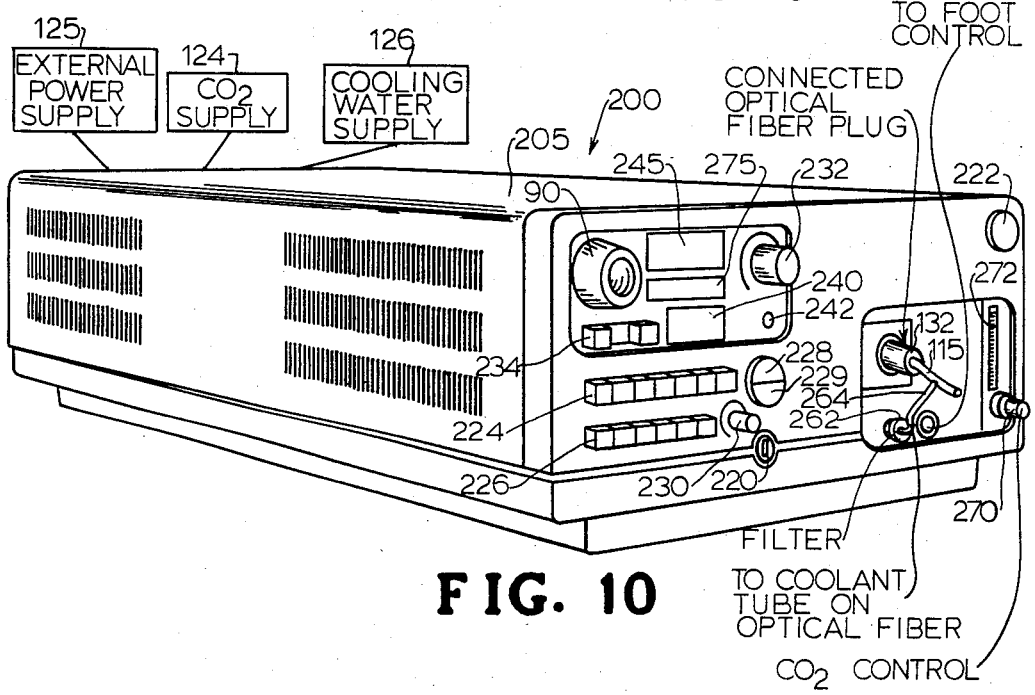
FIG. 10

LASER OPTICAL DELIVERY APPARATUS

DESCRIPTION

Cross Reference to Related Applications

The present application relates to optical delivery apparatus useful in conjunction with the fiber optic devices described in copending applications Ser. No. 437,288, filed Oct. 28, 1982, entitled "Laser Endocoagulator Apparatus"; Ser. No. 438,041, filed Oct. 15, 1982, entitled "Fiber Optic Laser Catheter"; Ser. No. 478,158, filed Mar. 23, 1983, entitled "Detachable Laser Optical Fiber Assembly And Method Of Adjustment"; and Ser. No. 437,289, filed Oct. 28, 1982, entitled "Disposable Hand Piece For Surgical Lasers".

TECHNICAL FIELD

The invention relates to apparatus for delivery of the laser discharge from the laser source to the site of application and is more specifically directed to medical laser optical delivery apparatus.

BACKGROUND ART

The use of lasers such as an argon-ion laser has become extremely significant in various fields of medicine. With the expanded number of medical applications, the medical profession has found itself dealing with many new kinds of procedures and operating conditions. Aside from having to determine the appropriate laser source for the desired absorption, reflection, scattering or transmission of the light by the tissue being exposed in the procedure, it has also become increasingly important to improve what is generally termed the optical delivery apparatus. More specifically, various improvements in devices for connecting the laser source to the fiber optics, for handling the fiber optics at the operating site, for minimizing infection and other contamination risk, and for controlling the amount of beam power delivered, both during standby and the aiming procedure as well as during the operating procedure have all become extremely important considerations. Significant improvements in optical delivery are represented by the various optical delivery devices described in the referred-to, previously-filed, copending applications. Interchangeable optical delivery assemblies utilizing such improvements is now recognized as a critical need and providing such interchangeable capability is an object of the invention. The invention also recognizes a need for additional improvements enabling the laser operator to observe signals representative of the actual power being sent to the distal end as well as to the actual power emitted by the proximal end of the fiber. Thus providing this capability becomes one object of the present invention. The invention also recognizes a need to provide a unified optical delivery apparatus in which focusing, beam splitting and filter lenses are readily accessible and easily replaced. Another need recognized by the present invention has been that of being able to more conveniently aim and control the laser beam while operating on a lower power level than has heretofore been possible. Thus, another object of the present invention is that of providing an improved optical delivery apparatus which provides such a low level power aiming capability.

Various types of laser light blocking and scattering devices have been known. However, with the advent of improved optical delivery devices such as those described in the referred-to copending applications, it has become increasingly important that the laser power be completely shut off or blocked in the situation in which there is, for example, no outgoing connection to optical fiber or when the operation is otherwise not ready to proceed. Thus, the availability of improved, remotely-controllable blocking and scattering shutters suited to interlock systems with interlock status display becomes significant. An improved blocking shutter, scattering shutter, outgoing fiber plug position sensor and scattering shutter position sensor, all constitute additional desired features that have been recognized and the achieving of an improved optical delivery apparatus with the mentioned as well as other features constitutes an object of the invention which along with other objects will become apparent as the description proceeds.

DISCLOSURE OF THE INVENTION

An improved optical delivery apparatus according to the invention is adapted to operate in conjunction with optical delivery devices such as those described in the referred-to copending applications but in an interchangeable form. More specifically, an argon-ion laser intended for medical application is used as an illustrative embodiment. In the conventional structure, the laser tube is mounted on a support structure with a pair of opposed wobble plates with associated mirror mounts.

The invention apparatus provides a unified assembly which attaches to one of the wobble plates for thermal tracking and in turn mounts various improved devices associated with the invention and also mounts interchangeable optical fiber plugs and fiber assemblies. Such improved devices include a beam splitter mounted in the path of the laser beam for providing a light source indicative of the power being delivered to the proximal end of the fiber optics. Another improved device forming part of the assembly is a receptacle for receiving a plug connected to the outgoing fiber optics and with means to sense correct positioning of the plug and therefore to sense correct positioning of the outgoing fiber optics. In conjunction with the outgoing fiber optics sensing arrangement, the improved assembly also provides a blocking shutter and a scattering shutter and a position sensor for the scattering shutter appropriately connected so that the laser beam can either be completely shut off when required or reduced to a low power level for aiming purposes prior to use of full power during the operating procedure. In the event of beam-fiber misalignment, a replaceable sealing filter-lens located between the shutters and the fiber optics confines any resulting vapors such that the vapors cannot contaminate the shutters.

Associated with the foregoing improvements forming part of the mentioned invention assembly, there is also provided a panel mounted light detector with a light receptacle and switching means enabling selective display of either the actual power being emitted at the distal end of the fiber optics or the actual power obtained through the mentioned beam splitter entering the proximal end of the fiber optics.

DESCRIPTION OF THE DRAWINGS

FIG. 4 is a rear elevation view of the improved optical delivery assembly viewed from a direction opposite to that of FIG. 3.

FIG. 4A is a view of FIG. 4 in reduced scale with certain portions removed for purpose of illustration.

FIG. 5 is a section view taken generally along line 5—5 of FIG. 3 with various components seen in FIG. 3 eliminated for simplifying the illustration.

FIG. 6 is a top plan view of the optical delivery assembly shown in FIG. 3.

FIG. 7 is an enlarged detailed section view of a beam splitter used in the invention.

FIG. 8 is a top plan elevation view of a scattering shutter used in the invention.

FIG. 9 is an enlarged detailed section view illustrating a screw mounting arrangement used for securing the lens retainer to the mounting block.

FIG. 10 is a front perspective view of a medical argon-ion laser constructed according to the invention.

BEST MODE FOR CARRYING OUT THE INVENTION

Those skilled in the art will appreciate from the following description that the optical delivery apparatus of the invention is applicable to many types of lasers including the argon-ion laser. Because of its application to numerous medical procedures for which the invention optical delivery apparatus offers significant advantage, a high-power, argon-ion medical laser is used as a representative embodiment of a type laser suited to the invention.

Figure 1:
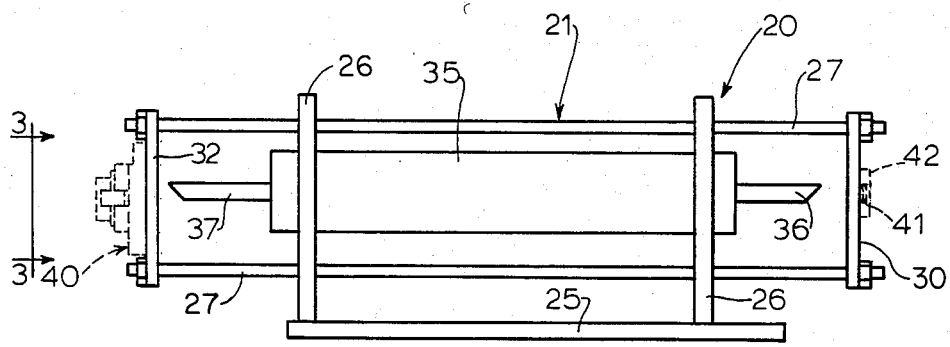
FIG. 1 is a side elevation view of a typical conventional mounting arrangement for an argon-ion laser tube and associated wobble plates and with the optical delivery assembly of the invention shown in dashed lines attached to a wobble plate at the anode end.
Figure 3:
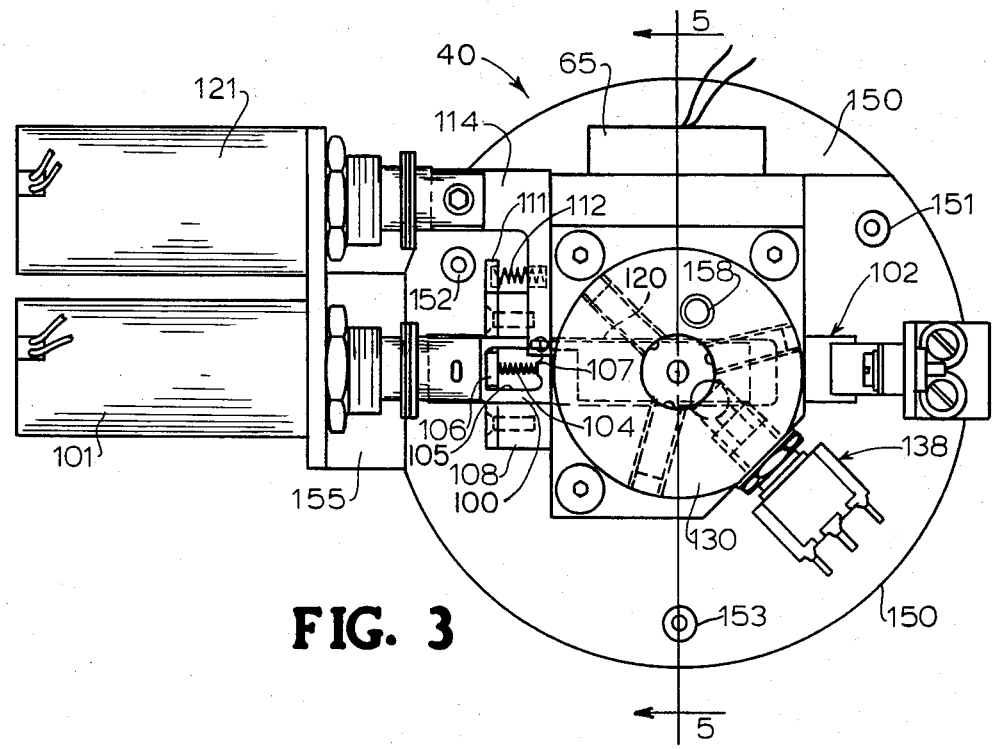
FIG. 3 is a front elevation view looking in the direction of lines 3—3 of FIG. 1 of the improved wobble plate mounted optical delivery assembly of the invention.

Making reference to FIG. 1 there is illustrated in simplified form, without illustrating any specific type of cooling, power delivery, anode or cathode configuration, the basic laser tube support structure 20 for an argon-ion laser 21 of the type sold by HGM, Incorporated, of Salt Lake City, Utah. Such structure typically includes a base plate 25, upright support plates 26, rods 27, and a pair of cooperative opposed end or wobble plates 30, 32. The laser tube 35 having a cathode end 36 and an anode end 37 is supported within the support structure 20. Wobble plates 30, 32 typically support transmission mirrors 41 on mirror mounts 42, and end plate and adjusting structure, not shown, for precisely adjusting both wobble plate and mirror positions. Once so adjusted, the wobble plates and mirrors track each other thermally.

The optical delivery apparatus of the invention is to a considerable extent built around the employment of an optical delivery assembly, generally designated 40 and shown in dashed lines in FIG. 1. Assembly 40 is attached to one of the wobble plates 32 and thereby tracks wobble plate 32 thermally. While illustrated as attached to the anode end, assembly 40 could be attached to either anode or cathode end or to other structure which tracks the laser mirror system thermally as do the wobble plates. The optical delivery assembly 40 supports a number of components related to the improved optical delivery apparatus of the invention. Once those skilled in the art appreciate the function and interrelation of such devices in the improved optical delivery apparatus of the invention, it will become apparent that the actual electromechanical structure could be made in any of a number of ways and still achieve the improved invention functions. Thus, the structure of the optical delivery assembly 40 as more fully illustrated in reference to FIGS. 2-9 should be taken as illustrative of what applicants regard as a practical, working preferred embodiment but with recognition that the construction of the optical delivery assembly 40 can vary substantially from that illustrated in the drawings and could also be applied to other than the argon-ion type laser used by way of example.

Figure 2:
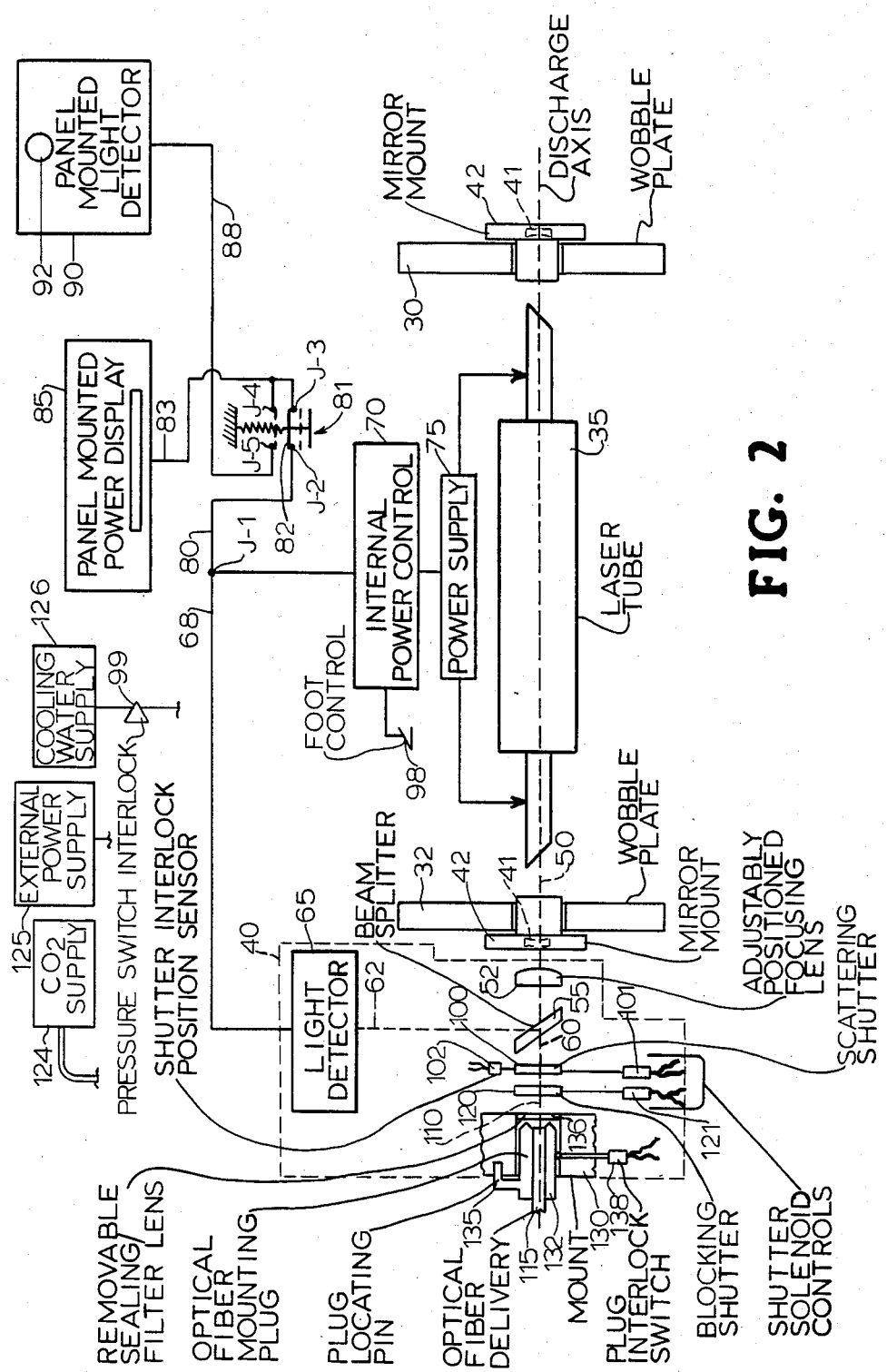
FIG. 2 is a schematic illustration of an improved optical delivery system according to the invention.

Prior to describing in detail the optical delivery assembly 40 and its construction, reference is made to a more general description of the overall optical delivery system of the invention in reference to FIG. 2 after which the description will turn to the construction details as illustrated in other drawings. Making reference to FIG. 2, the optical delivery assembly 40 of the invention which is attached to the wobble plate 32 acts as a means for supporting various devices in the laser beam path 50. One such device is an adjustably positioned focusing lens 52, also seen in FIGS. 4 and 5, which provides adjustable means for precisely focusing the beam relative to the fiber as more fully understood from later description. An additional advantage obtained is the ease with which the focusing lens 52 can be removed and replaced when necessary because of deterioration, beam damage, or otherwise.

Another element supported by the optical connector assembly 40 is a beam splitter 55, also seen in FIGS. 5 and 7, the purpose of which is to split the laser beam 50 into an ongoing beam 60 for transmission to the proximal end of the optical fibers as later described and a reference beam 62 which is converted by a light detector 65 into an appropriate electrical signal on line 68 connected to a junction J-1. Light detector 65 in the illustrated embodiment is mounted relatively close to the beam splitter lens 55 to reduce signal loss. At the junction J-1, the signal corresponding to reference light beam 62 is connected to the conventional internal power control 70 and power supply 75 schematically illustrated in FIG. 2 such that the electrical signal developed on line 68 corresponding to the split beam 62 can be used to regulate the power supplied to laser tube 35. Light beam 62 thus represents the power level of light beam 60 entering the optical fiber at the proximal end of the fiber. Display of this level enables the operator to control this power level going into the optical fiber utilizing the treatment power control shown in FIG. 11.

Junction J-1 connects through line 80 to junction J-2 and through contact 82 of pushbutton switch 81 and junction J-3 to line 83 in the solid line position of FIG. 2. Thus, with switch 81 positioned as indicated in FIG. 2, the power level corresponding to the electrical signal on line 68 by light beam 62 is visually displayed on the panel-mounted digital power display 85 diagrammatically illustrated in FIGS. 2, 10 and 11. When switch 81 is depressed, contact arm 82 of switch 81 assumes the dotted line position indicated in FIG. 2 which connects junctions J-4 and J-5 and line 88 to line 83. Line 88 is in turn connected to a panel-mounted light detector 90 having an appropriate aperture for insertion of the distal end of the optical fiber, thus allowing the output light level to also generate and display a power level on power display 85 indicative of the light output power at the distal end of the optical fiber. Since devices suitable for displaying power level according to light-generated electrical signal strength are well known in the art as well as devices for detecting light and developing a corresponding signal indicative of the power level associated with the light, further description of this aspect of the invention system is not deemed necessary. Thus, the description will now turn to other devices mounted on the optical delivery assembly 40.

Use of an argon-ion laser for medical procedures typically using a slit lamp or operating microscope requires that provision be made for aiming the light beam with a high degree of precision and at a power level sufficiently low to avoid interaction with the tissue involved in the operation. Additionally, it is imperative that all light from the laser tube be positively blocked under certain conditions as for example in the standby mode or in the event the optical fiber delivery system is not in place or, as another example, in the event the tube coolant is inoperative. It is also desirable that there be an appropriate interlock system to sense the position of whatever device is used to reduce the beam power or to block the beam to know that such devices are in position when required. The optical delivery assembly 40 thus provides a scattering shutter 100 controlled by solenoid 101 and associated with a position sensor 102 as further schematically illustrated in FIG. 2. Thus, as will be readily understood, shutter 100 provides a means for scattering the light and thus achieving a relatively low power level in beam 110 entering the optical fiber 115. In a similar manner, there is provided a blocking shutter 120 controlled by a solenoid 121 as further schematically illustrated in FIG. 2. Thus, except when blocking shutter solenoid 121 is energized, light beam 60 is effectively completely blocked from entering the optical fiber 115 whereas energizing of solenoid 121 acts to withdraw blocking shutter 120 and allows the light beam 60 to enter the optical fiber 115. Shutters 100 and 120 are both spring loaded.

To complete the generalized description of the optical delivery system of the invention in reference to FIG. 2, the optical delivery assembly 40 also includes a mounting block 130 for receiving an optical fiber connecting plug 132 having a positioning pin 135 snugly fitting plug positioning hole 158 for precisely locating the proximal end of the optical fiber 115 both longitudinally and rotatively with reference to the light beam 110 and with the correct positioning of plug 132 being subject to a plug interlock switch 138 also seen in FIG. 2. As one aspect of the invention, unless plug 132 is properly positioned so as to properly position the plug interlock switch 138, power supply 75 is made inoperative, i.e., no power is supplied to tube 35. Block 130 is preferably made of hardened stainless steel and hole 158 is bored with a high degree of accuracy.

From the foregoing, it can be seen that when the fiber optics connecting plug is of the type having a positioning pin 135, the plug must be installed correctly both as to its rotative position as well as its longitudinal position for the plug interlock switch 138 to indicate proper fiber alignment. Additionally, it will be seen that since blocking shutter 120 is normally in a blocking position energization of blocking shutter solenoid 121 effective provides a means for withdrawing blocking shutter 120 only in a medically-safe situation. Additionally, scattering shutter position sensor 102 provides an interlock device enabling sensing of scattering shutter 100 being in a scattering position as is desirable during beam aiming at low power level.

The use of a fiber optics positioning pin such as illustrated by plug 132 and pin 135 particularly advantageous when using a small diameter bundle of optical fiber, e.g., 50 to 100 millimeters. In other applications as illustrated in later-described FIG. 17, a locating pin is not required. However, the plug interlock switch 138 remains useful in sensing whether such a plug has been installed and properly positioned longitudinally. Thus, mounting block 130 and plug interlock switch 138 adapt to both the type of optical fiber plug having a positioning pin as well as the type which does not as best illustrated in later described FIG. 17.

The optical delivery system of the invention also adapts to use of optical fiber delivery devices in which a coolant gas, e.g., $CO_2$, is delivered to the operative site in conjunction with the laser beam as illustrated in copending application Ser. No. 438,041. A source of $CO_2$ gas 124 is thus schematically illustrated in FIG. 2 in conjunction with an associated external electrical power supply 125 and cooling water supply 126. The manner in which such $CO_2$ gas is monitored and dispensed in the present invention in conjunction with using a gas-cooled fiber optics plug and assembly such as disclosed in copending application Ser. No. 438,041 is later described in connection with the description of FIGS. 11 and 18. What is to be recognized here is that the optical delivery system of the invention not only adapts to the type fiber optics assembly which uses a coolant but also provides improved operator-controlled, panel-mounted means for controlling and dispensing such coolant.

The description will next proceed to some of the details of construction and operation of the various devices to which reference has just been made in connection with FIG. 2.

Thus, the immediately following description will be primarily directed to describing the physical construction of the adjustably positioned focusing lens 52, the beam splitter 55, the scattering shutter 100 and its controls, the blocking shutter 120 and its controls, and the optical fiber mounting block 130 with the associated plug interlock switch 138 and removable sealing-filter lens 136.

As best seen in FIGS. 3–6, the optical delivery assembly 40 incorporates a mounting block 150 which is secured by screws, not shown, to wobble plate 32 and which are mounted in holes 151–153. Mounting block 150 in turn mounts a bracket 155 on which are mounted the scattering shutter control solenoid 121 and the blocking shutter control solenoid 101 previously referred to in connection with FIG. 2.

The mirror mount 42 on wobble plate 32 (FIGS. 2 and 5) mounts within a cavity 162 in mounting block 150 and laser beam 50 (FIG. 2) focuses on the adjustably mounted focusing lens 52. Lens 52 is held in lens retainer 53 by a lens retaining ring 54. Lens retainer 53 is secured to mounting block 150 by a set of three screws 56–58 (FIG. 4). An enlargement of one of the mounting screws 57 is shown in FIG. 9 in conjunction with the beveled washer 59 and flat washer 61 which allow lens retainer 53 to be accurately and securely positioned and maintained on mounting block 150 while still allowing sufficient movement for final adjustments. Additional extremely precise adjustments are also obtained by means of using the adjusting screws 71–74 (FIG. 4) which engage the corresponding flat surfaces 76–79. Adjusting screws 71–74 are used after the optical delivery assembly 40 of the invention is attached to wobble plate 32 which thus provide external access through which the final adjustments are made to the focusing system.

As previously mentioned, the optical delivery assembly 40 also serves as a means for supporting the beam splitter 55 from which the reference beam 62 (FIG. 2) is obtained which allows the power entering the proximal end of the fiber optics to be displayed on the power display 85. Beam splitter 55 comprises a beam splitter lens 92 (FIG. 7) secured by a snap ring 93 fitted in the beam splitter retainer 94 secured by screws 97, 98. Thus, the beam splitter 55 is rigidly secured relative to the mounting block 150 and the focusing lens 52. The split beam 62 is directed through cavities 95, 96 to a conventional light detector 65 with associated circuitry, not shown, for developing a signal on line 68 indicative of the power level of the split beam 62. Thus, the power of the beam entering the fiber optics can be displayed on the power display 85 as previously described.

The optical delivery assembly 40 also provides support for the scattering shutter 100 and the blocking shutter 120. The scattering shutter electrically actuated solenoid 101 and the blocking shutter electrically actuated solenoid 121 are both mounted on bracket 155 secured to mounting block 150. Solenoid 101 connects directly to the scattering shutter 100 and is normally positioned such that the scattering lens 103 (FIG. 8) is held in the path of the laser beam which passes through the beam splitter 55 except when solenoid 101 is energized. Scattering lens 103 is preferably a frosted or ground ultraviolet grade quartz so as to promote scattering rather than absorption of the light.

Figure 12:
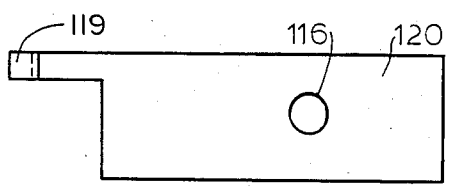
FIG. 12 is a top plan elevation view of a blocking shutter used in the invention.
Figure 13:
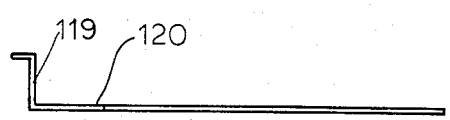
FIG. 13 is a side elevation view of the blocking shutter of FIG. 12.
Figure 14:
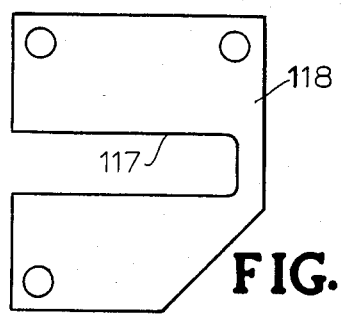
FIG. 14 is a top plan elevation view of the blocking shutter shim and guide.
Figure 15:
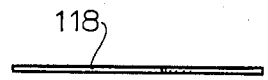
FIG. 15 is a side elvation view of the blocking shutter shim of FIG. 14.
Figure 16:
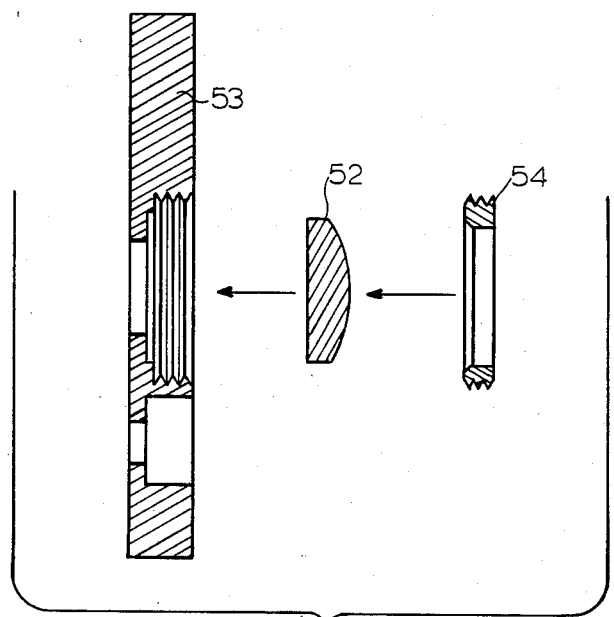
FIG. 16 is an enlarged exploded section view of the sealing lens-filter assembly.

Tension spring 104 in slot 105 is held between bracket arm 106 (FIG. 3) in slot 105 and protrusion 107 (FIG. 8) to spring load lens 103 on scattering shutter 100. Bracket arm 106 forms part of a spring retainer bracket 108 secured to mounting block 150 and which also includes another bracket arm 111 for retaining one end of another tension spring 112. Spring 112 bears against an L-shaped arm 114 (FIG. 12) which connects blocking shutter control solenoid 121 to arm 119 (FIG. 13) of the blocking shutter 120. Blocking shutter 120 slides in a slot 117 formed in a shim 118 (FIG. 14). Thus, blocking shutter 120 is always forced into a fully blocking position except when its control solenoid 121 is energized. However, when solenoid 121 is energized, the beam is allowed to pass through an aperture 116 (FIG. 12) formed in blocking shutter 120. In general, it can be stated that the energization of blocking shutter control solenoid 121 is detected by suitable circuitry and is energized only when it is safe to operate the laser. Thus, appropriate interlocks are provided such that control solenoid 121 is not energized whenever the optical fiber plug 132 is not in place, whenever the laser cooling system is not operative as indicated by pressure actuated switch 99 schematically illustrated in FIG. 2, or whenever the power level is indicated to be excessive, either by the power display 85 indicating excessive power at the proximal end of the fiber optics, or by light and signal generating detector 90 indicating excessive power at the distal end of the fiber.

As an additional safety feature, a suitable light detecting position sensor 102 is supported by a bracket 105 on mounting block 150. Sensor 102 develops a signal, the character of which is dependent on whether scattering shutter 100 is or is not retracted. Such signal is then fed to appropriate interlock circuitry so that when shutter 100 is sensed as not being properly positioned either for scattering during the aiming mode or for passing the laser beam through aperture 108 (FIG. 8) when shutter 100 is withdrawn. Foot control switch 98 (FIG. 2) is suitably connected to control energization of scattering shutter solenoid 101.

In the event of misalignment of the optical delivery system with the optical fiber which is being used to transmit the laser beam to the operating site, there is a strong likelihood of damage to both the optical delivery system and to the receiving optical fiber. Recognizing this problem, there is also mounted in the mounting block 130 a removable sealing and filter lens 136 made of ultraviolet grade guartz and the purpose of which is to provide a means for protecting the distal or input end of optical fiber in the event of such misalignment. Lens 136 is mounted in a receptacle 139 with external threads 140 and with a snap ring 141 securing lens 136 in position. Receptacle 139 is easilY removed and replaced by removing the optical fiber mounting plug 132 and inserting a tool which can be expanded to grip the internal surface 137 of receptacle 139 and rotating the tool to unscrew the receptacle 139. This tool has access through bore.

When the optical fiber mounting plug 132 is properly positioned and the locating pin 135 properly inserted, the plug interlock switch 138 will be positioned so as to indicate that the optical fiber 115 is positioned to receive the laser beam 60. Thus, when the blocking shutter 120 is retracted and the scattering shutter 100 is in a light scattering position, a relatively low level laser beam power will be transmitted to the optical fiber 115 for aiming purposes and without risk of tissue damage. Once such aiming has been accomplished, the operator using foot switch 98 (FIG. 2) connected to the receptacle 145 (FIG. 11) can through control circuitry, not shown, cause scattering shutter solenoid 101 to be energized, scattering shutter 100 withdrawn and full power to be applied to the optical fiber 115. However, if locating pin 135 is not appropriately positioned or if the plug interlock switch 138 does not indicate that the optical fiber mounting plug 132 is properly positioned, the mentioned foot switch 98 is ineffective and the circuitry is designed so as to deenergize the blocking shutter control solenoid 121 thus allowing the blocking shutter 120 to completely block the laser beam 60.

Figure 17:
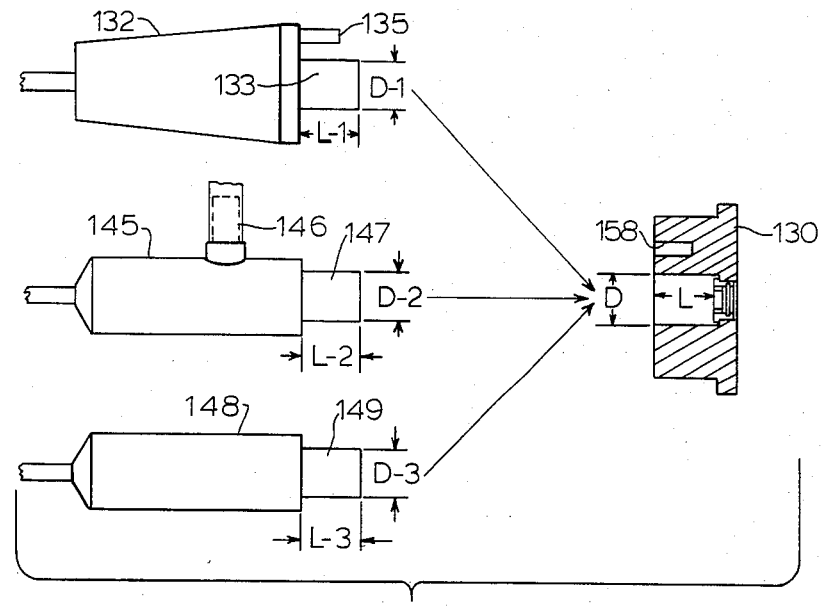
FIG. 17 is a schematic diagram illustrating three types of precision-formed optical fiber plug assemblies adapted to be used interchangeably with the optical delivery assembly of the invention.

The mentioned copending applications establish the fact that optical fiber connecting plugs such as plug 132 can be molded of suitable plastic and with sufficient precision to meet the very critical need for precise beam alignment. Building on this prior discovery, FIG. 17 illustrates pin type plug 132 fitted with positioning pin 135 and fiber guide 133 standardized with respect to precision-formed dimensions L-1, D-1 mating precision-formed dimensions L and D of mounting block 130. In a similar manner, the gas-cooled-type plug 145 having the gas cooling-line 146 is standardized as to dimensions L-2, D-2 of fiber guide 147 mating dimensions L and D. In a further illustration of interchangeability, the non-pin and non-gas cooled-type plug 148 is provided with dimensions L-3, D-3 and fiber guide 149 mating dimensions L and D of mounting block 130. Thus, the invention assembly provides the extremely advantageous feature of interchangeable fiber optic assemblies with standard size and precise snug fitting plugs.

As perhaps best illustrated in FIG. 2, it can be seen that the optical delivery assembly 40 provides among other advantages the advantage of ensuring that the focusing lens 52, the beam splitter 55, the scattering shutter 100, the blocking shutter 120 the sealing-filter lens 136 and the proximal end of the optical fiber 115 are all maintained in precise alignment which is coordinated to track the thermal shift of the laser mirror system by reason of the mounting block 150 being rigidly secured to the wobble plate 32. Another significant advantage of the described optical delivery assembly 40 is that all of the mentioned components, i.e., the focusing lens 52, the beam splitter 55, the scattering shutter 100, the blocking shutter 120, the plug mounting block 130, the scattering shutter position detector 102, the light detector 65, and the plug interlock switch 138, as well as the control solenoids 101, 121, can all be mounted in an extremely compact assembly suited to manufacture as a subassembly for quick attachment to and quick removal from the wobble plate 32. This compactness in turn has led to achieving an extremely compact, highly portable argon-ion laser housed in a relatively small cabinet which in one embodiment was approximately 16 inches wide by 8 inches high by 31 inches long as further schematically demonstrated in FIGS. 10 and 11.

Figure 11:
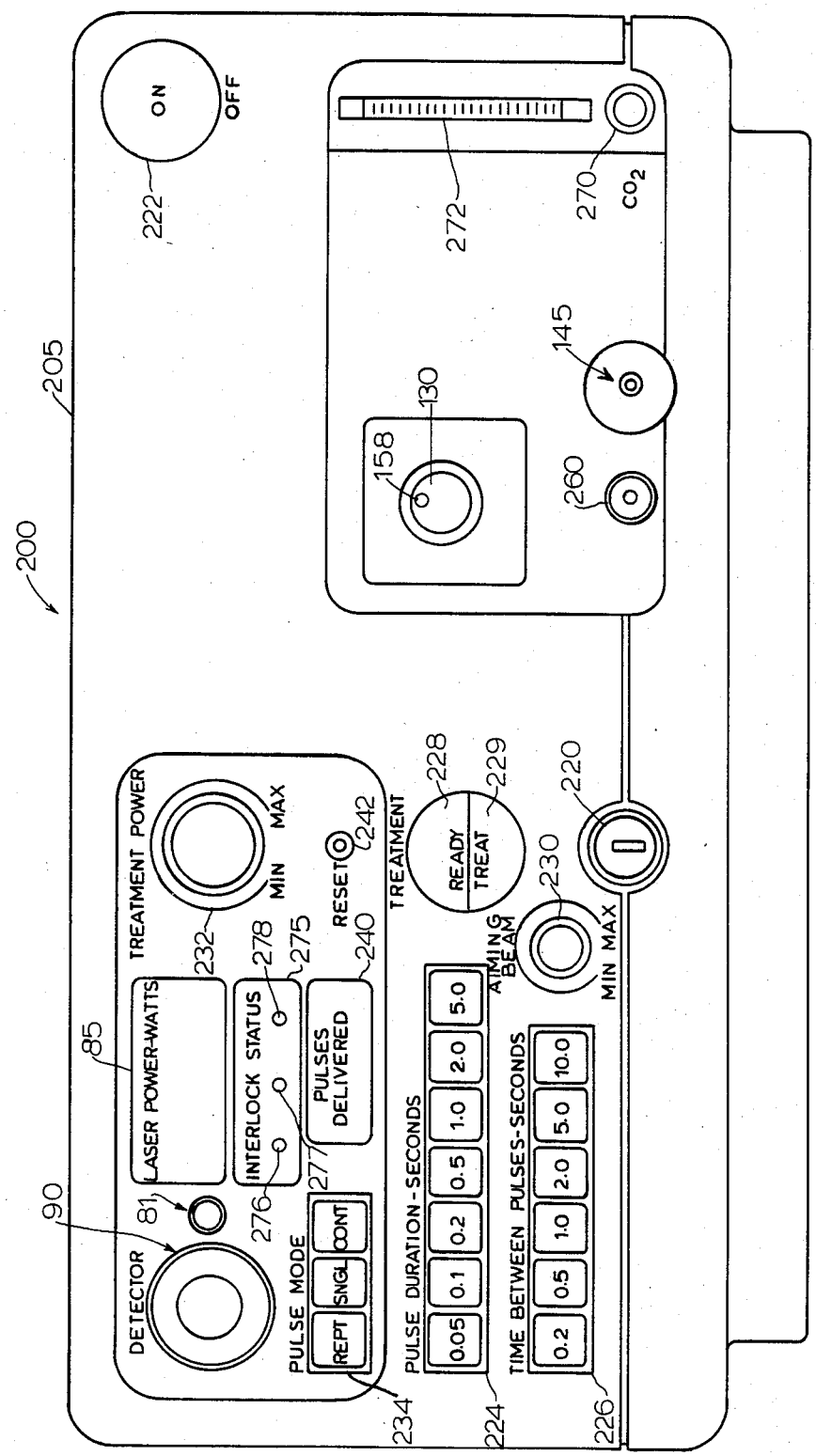
FIG. 11 is an enlarged front elevation view of the laser cabinet illustrated in FIG. 10 showing typical control labels and connection points.
Figure 18:
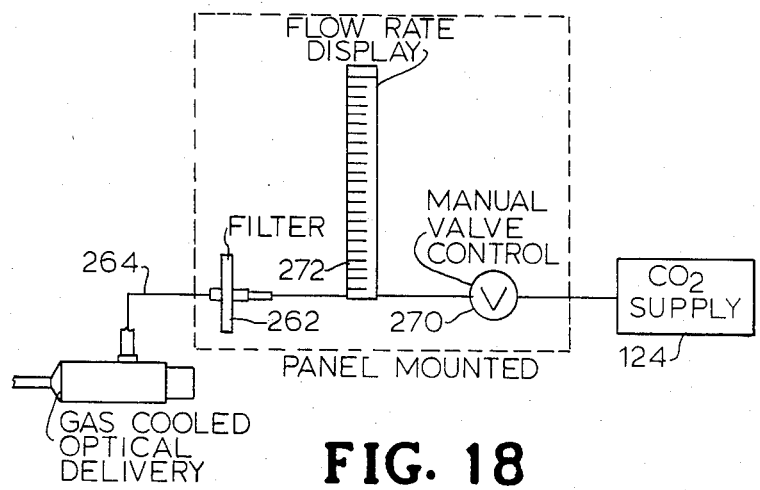
FIG. 18 is a schematic diagram of a $CO_2$ flow system used with the invention.

The invention system also lends itself to use of those types of fiber optics in which a gas such as $CO_2$ is directed to the operating site as further schematically illustrated in FIGS. 10, 11 and 18.

In FIGS. 10 and 11 there is illustrated a cabinet and control arrangement providing a medical argon laser 200 representative of the type laser in which the optical delivery assembly 40 and related components of the invention can be easily incorporated to provide a complete laser instrument. It will, of course, be understood that the laser 20 schematically shown in FIG. 1 together with appropriate power supplies, controls, cooling structure and interconnecting power, control, water and gas lines are suitably housed in the cabinet 205 seen in FIGS. 10 and 11. All user controls and indicators, with the exception of foot switch 98 and a rear panel-mounted circuit breaker, not shown, are mounted on the front panel as seen in FIGS. 10 and 11. As schematically illustrated in FIG. 10, the laser 200 is connected to the external power supply 125, typically single-phased AC, the $CO_2$ coolant gas supply 124 and the cooling water supply 126.

Referring specifically to the control panel illustrated in FIG. 11, there is provided a key-operated lock 220 providing general access, an on-off switch 222, a push-button-type pulse duration control and display 224, a time between pulses control and display 226, a ready status display 228, treat switch 229, an aiming beam power control 230, a treatment power control 232, a pulse mode control and display 234 providing for repeat, single and continuous pulse modes, a display 240 for displaying pulses delivered with a count reset 242 for cancelling display 240, the previously-mentioned switch 81 and display 85 for displaying distal end or proximal end beam power in the fiber, the previously-mentioned light detector 90 for receiving light emitted by the distal end of the optical fiber, the electrical receptacle 145 for receiving a cable connection to the foot switch 98 and the gas receptacle 260 suited to mounting an in-line sterile filter 262 (FIG. 10). A gas line 264 connects to the filter 262 and extends to the coolant tube associated with the fiber optics as further illustrated in FIG. 18. Mounting block 130 fitted with the pin-positioning hole 158 is shown in FIG. 10 in the manner in which it receives the fiber optics connecting plug 132 and in the illustrated example is also shown associated with the $CO_2$ coolant line 264. The $CO_2$ flow is adjusted by a valve control 270 and the flow rate is indicated on visible gauge 272. Interlock status is indicated by an interlock display 275 having a light display 276 for the scattering shutter interlock sensor 102, a light display 277 for the fiber plug interlock switch 138, and a light display 278 for the coolant flow interlock (not shown).

In summary, some of the advantages of the optical delivery system of the invention can be stated as follows:

1. The invention system enables use of a wide range of
interchangeable fiber optics. Fiber optic diameters of 100, 200 and 600 microns have been successfully tested. Thus, when optical fiber of one diameter is dirty or broken or needs to be changed for optical fiber of another diameter, this can be quickly accomplished with the invention system of interchangeable plugs and fibers.

2. A substantial reduction in overall size of the laser and its cabinet enclosure has been achieved. Thus, the invention laser is highly portable and can be transported on a suitable cart.

3. A beam splitter associated with a panel-mounted power meter enables selective display of either the power going into the proximal end of the fiber or the power going out the distal end of the fiber.

4. The removable sealing-filter lens isolates fiber vapors from the shutters when the fiber is overheated to protect the critical laser optical elements and when this lens is itself damaged it can be readily replaced.

5. Thermal tracking of the invention optical delivery assembly components, particularly the focusing lens, with the laser mirror system is assured by reason of utilizing a wobble plate to support the invention assembly.

6. Precise, secure and accessible adjustment of the focusing lens is provided.

7. Protective and displayed interlocks are provided for the scattering shutter, optical fiber plug and coolant flow.

8. Beam aiming is protected and facilitated by the position detected scattering shutter.

9. Optional use of an easily connected and controlled filtered coolant gas, i.e., $CO_2$ is provided.

10. Various components such as the focusing lens, beam splitter and sealing-filter lens are mounted in such a way as to be easily replaceable when damaged or otherwise worn.

11. A compact subassembly is obtained which can be easily attached and removed from the wobble plate and which in one integrated assembly incorporates the focusing lens, the beam splitter and associated detector, both the scattering and blocking shutters, the scattering shutter sensor, both shutter control solenoids, the optical fiber plug mounting block and the plug interlock switch.

12. Optical alignment after the optical delivery assembly of the invention is attached to the wobble plate is readily achieved.

13. Location of the foot switch cable connection on the front panel enables other operations such as coolant water flow to be made dependent on such foot switch connection having been first made.

14. The front panel-mounted, plug-receiving mounting block, i.e., mounting block 130, facilitates making other conditions, e.g., energizing the "Ready" lamp, dependent on the plug being installed and the plug interlock switch 138 actuated.

15. Use of the standardized plug D and L dimensions illustrated by FIG. 17 enables a variety of optical plugs to be used with mounting block 130 and where precise alignment is required for small diameter fiber in conjunction with the alignment pin 135.

16. Independently spring-loaded and solenoid-controlled blocking and scattering shutters are provided enabling the beam to be selectively blocked or scattered as required in a uniquely simplified system.

What is claimed is:

1. A laser system comprising:
   (a) a laser having a tube and mirror laser beam generating system mounted on base structure and at each of anode and cathode ends of said tube and mirror system a wobble plate surrounding the beam path and supporting a transmission mirror forming a part of said system, said wobble plate being mounted so as to track thermal drift of the system's optical alignment;
   (b) an optical delivery assembly, comprising:
      (i) a first mounting block providing a cavity adjacent and removably secured to a selected said wobble plate for corresponding thermal tracking thereof and having an opening extending therethrough for passing said laser beam;
      (ii) focusing means mounted on said first mounting block including a focusing lens mounted within said cavity for focusing said laser beam with means separately supporting said focusing lens and accessible externally of said cavity for precisely adjusting said focusing lens with respect to said beam;
      (iii) beam splitting means mounted on said first mounting block and located in the path of said laser beam for providing a split off beam directed away from the path of said laser beam;
      (iv) first circuitry means mounted on said first mounting block for detecting said split off beam and developing an electrical signal responsive to the level thereof;
      (v) a scattering shutter slidably mounted on said first mounting block and having a first normal position with filtering means positioned for scattering said laser beam and a second withdrawn position with an aperture positioned for passing said laser beam;
      (vi) first sensing and display means including means dependent on the correct position of said scattering shutter for sensing such position and associated means for remotely displayed such correct shutter position:
      (vii) first controllable electric solenoid actuator means mounted on said first mounting block and linked to said scattering shutter and effective when energized to withdraw said scattering shutter from said first to said second position;
      (viii) a blocking shutter slidably mounted on said first mounting block and having a first normal position with a portion thereof positioned for blocking said laser beam and a second withdrawn position with an aperture positioned for passing said laser beam;
      (ix) second controllable electric solenoid actuator means mounted on said first mounting block and linked to said blocking shutter and effective when energized to withdraw said blocking shutter from its said first position to its second position;
      (x) a removable filter lens mounted on said first mounting block at a position effective to pass said laser beam dependent on said laser beam first having passed through both said shutters;
      (xi) auxiliary structure comprising an auxiliary mounting block secured to said first mounting block and providing a first bore with precision-formed depth and diameter adapted for receiving a mating plug and aligning connected optical fiber having the proximal end enclosed by said plug and locating said proximal end immediately adjacent said filter lens, said filter lens being removably mounted in a second bore formed in said auxiliary mounting block;
      (xii) an optical plug and optical fiber assembly including a said mating plug adapted to be inserted and snuggly fitted in said first bore to a predetermined depth and an assembly of optical fiber operatively associated with said plug and with the proximal end thereof adapted to be aligned with said beam after passage through said filter lens when said plug is inserted in said first bore for transmitting said laser beam to the distal end of said fiber for utilizing said beam at a selected operative site; and
      (xiii) second sensing and display means dependent on the correct longitudinal position of said plug for sensing said plug position in said first bore and associated means for remotely displaying such correct plug position; and
   (c) a cabinet housing said laser and optical delivery assembly in a manner exposing said first bore, said scattering shutter and plug position displays to the operator of said laser.

2. In a laser as claimed in claim 1:
   (a) wherein said auxiliary mounting block includes a pin positioning hole parallel to and radially offset from said first bore; and
   (b) said plug includes a pin member mating said positioning hole enabling the proximal end of said optical fiber attached to said plug to be precisely and selectively positioned in said first bore, both longitudinally and rotatively.

3. In a laser as claimed in claim 1:
   (a) wherein said cabinet provides a front control panel mounting said scattering shutter and plug position displays; and (b) including means for sensing coolant pressure and displaying on said panel a signal indicative of the correctness of such pressure.

4. In a laser as claimed in claim 1 including second circuitry means providing selective display of either the power related to sais split off beam or the power emitted by the distal end of said assembly of fiber associated with said plug.

5. In a laser as claimed in claim 1 including means to spring load both said scattering and blocking shutters into normally respective scattering and blocking positions.

6. In a laser as claimed in claim 4 wherein:
 (a) said cabinet provides a front control panel; and
 (b) said second circuitry means includes:
  (i) a light receptacle mounted on said control panel adapted to receive the distal end of said fiber;
  (ii) first converter means associated with said receptacle for developing a first signal representative of the power level of light received by said receptacle;
  (iii) second converter means associated with said beam splitting means for developing a second signal representative of the power level of said split off beam;
  (iv) display means on said front panel for displaying either said power level; and
  (v) manual switching means mounted on said panel and connected for selectively receiving either said first or second signal and selectively displaying the corresponding power level.

7. In a laser as claimed in claim 1 wherein said laser comprises an argon ion gas laser.

8. In a laser as claimed in claim 1 wherein said plug and said assembly of fiber are adapted for being connected to a source of coolant gas and including a source of coolant gas operatively associated with said laser and a front control panel forming part of said housing and means mounted on said panel for controlling and monitoring the flow of said gas.

9. In a laser having a tube and mirror laser beam generating means mounted on a base structure and at each of the anode and cathode ends thereof an optical alignment thermal tracking wobble plate through which the laser beam passes, in combination:
 (a) an optical delivery assembly, comprising:
  (i) a mounting block removably secured to and thermally tracking a selected said wobble plate and having an opening extending therethrough for passing said laser beam;
  (ii) first beam control means mounted on and thermally tracking said block for focusing, filtering and selectively blocking and scattering said beam while passing therethrough; and
  (iii) second optical fiber mounting means associated with and thermally tracking said mounting block providing a precision formed bore adapted for being axially aligned with the path of said beam after passage through said first beam control means and for receiving in snug-fit relation a plug precisely mating said bore and mounting optical fiber for transmitting said beam to a site of use.

10. In a laser as claimed in claim 9 including a selected number of plug-filter assemblies each having a plug mated to snugly fit said bore and an optical fiber assembly unique with respect to the other said optical fiber assemblies in said number.

* * * * *